United States Patent
Wu et al.

(10) Patent No.: US 6,458,085 B1
(45) Date of Patent: Oct. 1, 2002

(54) METHOD AND APPARATUS FOR OSCILLOMETRIC BLOOD-PRESSURE MEASUREMENT

(75) Inventors: Shu-Mei Wu; Xing Ou-Yang, both of Taipei; Yeong-Dar Chen, Kaohsiung; Tung-Chuang Jan; Chao-Wang Chen, both of Taipei, all of (TW)

(73) Assignee: Taidoc Corp., Ltd., Taipei (TW)

( * ) Notice: Subject to any disclaimer, the term of this patent is extended or adjusted under 35 U.S.C. 154(b) by 21 days.

(21) Appl. No.: 09/708,468

(22) Filed: Nov. 9, 2000

(30) Foreign Application Priority Data

Sep. 1, 2000  (TW) ............................................. 89117854

(51) Int. Cl.$^7$ ................................................. A61B 5/02
(52) U.S. Cl. ........................ 600/494; 600/493; 600/490
(58) Field of Search ................................. 600/493, 494, 600/495, 496, 492, 490, 481

(56) References Cited

U.S. PATENT DOCUMENTS

| | | | | |
|---|---|---|---|---|
| 4,796,184 A | * | 1/1989 | Bahr et al. | 600/492 |
| 4,917,116 A | * | 4/1990 | LaViola et al. | 600/494 |
| 4,972,840 A | * | 11/1990 | LaViola et al. | 600/494 |
| 5,094,244 A | * | 3/1992 | Callahan et al. | 600/490 |
| 5,551,438 A | * | 9/1996 | Moses | 600/485 |

* cited by examiner

Primary Examiner—Kevin Shaver
Assistant Examiner—Navin Natnithithadha
(74) Attorney, Agent, or Firm—Rabin & Berdo, P.C.

(57) ABSTRACT

A method and an apparatus for oscillometric blood-pressure measurement taking heart pulses for reference to determine the systolic and diastolic pressure are disclosed. The cuff is merely inflated to a cuff pressure above the mean arterial pressure of the artery. Therefore, the inflation pressure of the cuff to be pumped much higher than the normal systolic pressure of the conventional method can be prevented. A comfortable systolic and diastolic pressure determination method applying fuzzy control is achieved.

5 Claims, 3 Drawing Sheets

METHOD AND APPARATUS FOR OSCILLOMETRIC BLOOD-PRESSURE MEASUREMENT

CROSS-REFERENCE TO RELATED APPLICATION

This application incorporates by reference Taiwan patent application Serial No. 8,9117,854, filed Sep. 1, 2000.

BACKGROUND OF THE INVENTION

1. Field of Invention

The present invention relates in general to an oscillometric non-invasive method and apparatus for measuring blood pressure, and more particularly to a method and apparatus which take heart pulses for reference to determine the systolic and diastolic pressure.

2. Description of Related Art

The heart of human being is like a pump and the muscles of the heart periodically contract to force blood through the arteries of the human. As a result, irregularly-shaped pressure pulses exist in theses arteries and cause them to flex or oscillate. The base line pressure for these pulses is known as the diastolic pressure and the peak pressure for these pulses is known as the systolic pressure. A further pressure value, known as the "mean arterial pressure" (MAP) represents a time-weighted average of the blood pressure.

In the past, various techniques and devices have been used for measuring one or more of these blood pressure values. The most common method involves applying a pressure cuff about the upper arm of the human and inflating it so as to stop the flow of blood in the brachial artery. The pressure is then slowly relieved while a stethoscope is used on the distal portion of the artery to listen for pulsating sounds, known as Kortotkoff sounds, that accompany the reestablishment of blood flow in the artery. As the pressure in the cuff is reduced further, the Korotkoff sounds eventually disappear. The cuff pressure at which the Korotkoff sounds first appear during deflation of the cuff is a measure of the systolic pressure and the pressure at which these sounds disappear is a measure of the diastolic pressure. This method of blood pressure detection is generally known as the "auscultatory method".

Various devices are well known in the prior art for automatically performing blood pressure measurement by the auscultatory method. These devices employ a pump to automatically inflate a pressure cuff and a microphone to convert the Korotkoff sounds into electrical signals which are easily detected by various types of circuits. Other techniques have also been used to detect blood pressure from outside the subject's body, e.g., via Doppler shifts in ultrasonic waves reflected by the artery wall. In addition, there are intrusive devices that are inserted directly into the blood vessels for measurement of the pressure. However, the most commonly used method for measuring blood pressure, other than the auscultatory method, is the "oscillometric method".

The oscillometric technique is based on the fact that the pumping of blood through the arteries by the heart causes the arteries to flex. Even in the area adjacent to or within a pressure cuff applied to the arm of a human, these pressure variations exist. In fact, the pressure variations will pass from the artery through the arm of the human with attenuation and into the pressure cuff itself. While these pressure variations are small compared to the typical pressure applied by the cuff, they are nevertheless detectable by a transducer located to measure the pressure within the cuff. It has been found that these pulses, called "complexes", have a peak-to-peak amplitude which is minimal for applied cuff pressures above the systolic pressure and below the diastolic pressure. The amplitude of these complexes, however, rises to a maximum value. Physiologically, the cuff pressure at this maximum value approximates the MAP. It has further been found that the complex amplitudes of cuff pressures equivalent to the systolic and diastolic pressures have a fixed relationship to this maximum value. Thus, the oscillometric method is based on measurements of detected complex amplitudes at various cuff pressures.

However, the above-mentioned oscillometric method has drawbacks in that the inflation pressure of the cuff must to be pumped much higher than the normal systolic one. For example, the pressure is generally about 180 mmHg to 240 mmHg for ensuring the detection of the blood pressure value in specific cases of high blood pressure. Users thus always suffer from uncomfortable measurement while inflating the cuff for a period of time. The continuous contraction of the cuff will cause pain, especially for obese patients, and even further hurt users. On the other hand, the conventional measuring is ineffective because the normal systolic pressure is around 130 mmHg and the much higher inflation pressure is needed in case of an exception.

SUMMARY OF THE INVENTION

Therefore, it is an object of the present invention to provide a method and an apparatus for performing oscillometric blood-pressure measurements comfortably and accurately.

According to the above object, the blood pressure determining method includes, (a) applying a blood pressure cuff about a subject's limb containing an artery; (b) inflating the cuff to a cuff pressure above the mean arterial pressure of the artery; (c) reducing the cuff pressure to permit an increasing flow through the progressively less occluded artery; (d) monitoring arterial counterpressure pulses and oscillations at each pressure reducing step; (e) converting the counterpressure oscillations to voltage signals; (f) processing the voltage signals into a sequence of peak amplitudes enveloped to obtain a curve containing a maximum value; (g) determining a diastolic pressure and a mean arterial pressure based upon the curve; and (h) determining a systolic pressure based upon the diastolic pressure, the mean arterial pressure and the counterpressure pulses.

In another aspect, the blood pressure determining apparatus includes, (a) an inflatable and deflatable cuff; (b) controlling means, for controlling cuff pressure so as to inflate the cuff to a maximum cuff pressure above the mean arterial pressure of a detected subject; (c) a monitoring means, for monitoring arterial counterpressure pulses and oscillations at each of the cuff pressure deflating process; (d) pressure transducer means, coupled to the cuff for converting the counterpressure oscillations to voltage signals; (e) a processing means, for processing the voltage signals into a sequence of peak amplitudes at each pressure deflating process, the sequence being enveloped by a curve containing a maximum value; and (f) determining means, for first determining a diastolic pressure and a mean arterial pressure based upon the curve and then determining a systolic pressure based upon the diastolic pressure, the mean arterial pressure and the counterpressure pulses.

The predicted mean arterial pressure can be obtained by further monitoring arterial counterpressure oscillations at each pressure inflating step. The systolic pressure determining step further computes the systolic pressure based upon the counterpressure pulses monitored around the mean arterial pressure.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become fully understood from the detailed description given hereinbelow illustration only, and thus are not limitative of the present invention, and wherein.

DETAILED DESCRIPTION OF THE INVENTION

Figure 1:
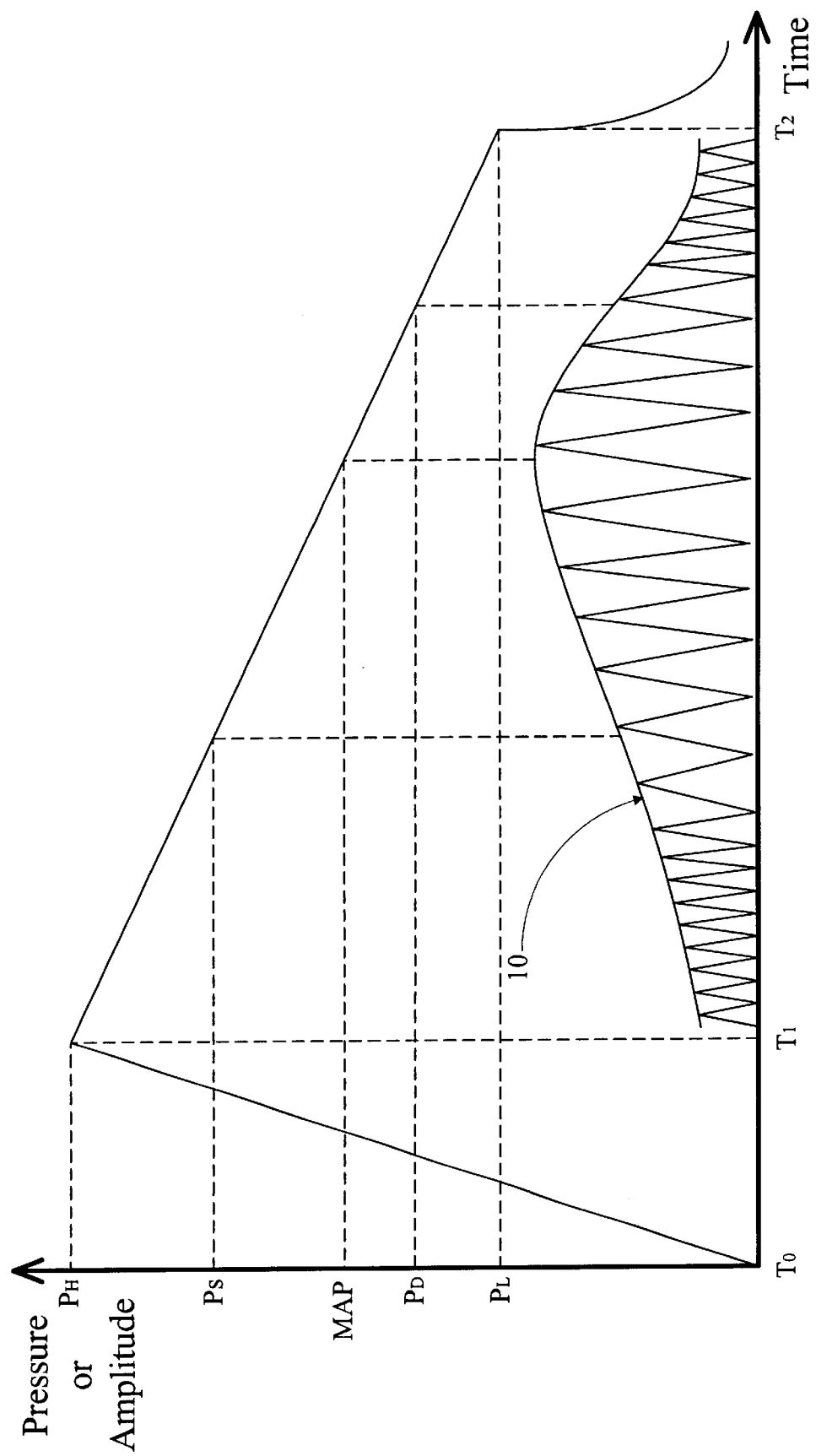
FIG. 1 shows two superimposed graphs of cuff pressure versus time and oscillation amplitudes versus time respectively according to the conventional method.

Referring to FIG. 1, the upper graph illustrates a typical cuff pressure/time graph of an oscillometric method of measuring blood pressure. At a time $T_0$, a pressure cuff that is applied to a subject's limb containing an artery, such as a human being's arm, is inflated to the pressure $P_H$ above the systolic pressure $P_S$, thereby occluding the artery. The highest $P_H$ value at time $T_1$, in general, is selected to be much higher than a normal $P_S$ value, such as 180 mmHg or above, to ensure the blood-pressure measuring device can be available for all users; otherwise, a patient with hypertension may suffer from miss-detection of his blood pressure. Next, during the time $T_1$ to $T_2$, the cuff pressure is deflated to permit an increasing flow through the progressively less occluded artery and at each pressure the arterial counterpressure oscillations are monitored. Accordingly, the cuff pressure complexes are measured after such pulses begin. After suitable filtering and amplification, corresponding oscillation peaks are obtain and depicted as an envelope 10 of the lower graph of FIG. 1, which illustrates a typical oscillation amplitude/time graph. As deflating of the cuff continues, the oscillation peak amplitudes will normally increase from a lower level to a relative maximum and, thereafter, will decrease. The cuff pressure at which the amplitude has a maximum value, labeled MAP in FIG. 1, is normally representative of the mean arterial pressure. Finally, at a time $T_2$, the pressure $P_L$ is reduced below the diastolic pressure $P_D$. Usually the $P_L$ value is sufficiently lower than a normal $P_D$ value, and the cuff is then entirely deflated to finish the whole measurement.

Prior improvements have always focused on how to accurately obtain the counterpressure oscillations during the cuff deflation process, and different calculation approaches to determine the systolic and diastolic pressure according to the mean arterial pressure. However, all of the prior methods for inflating the cuff are based upon a consideration of the systolic pressure. Therefore, it then cannot properly solve the uncomfortable contraction while measuring blood pressure.

Figure 2:
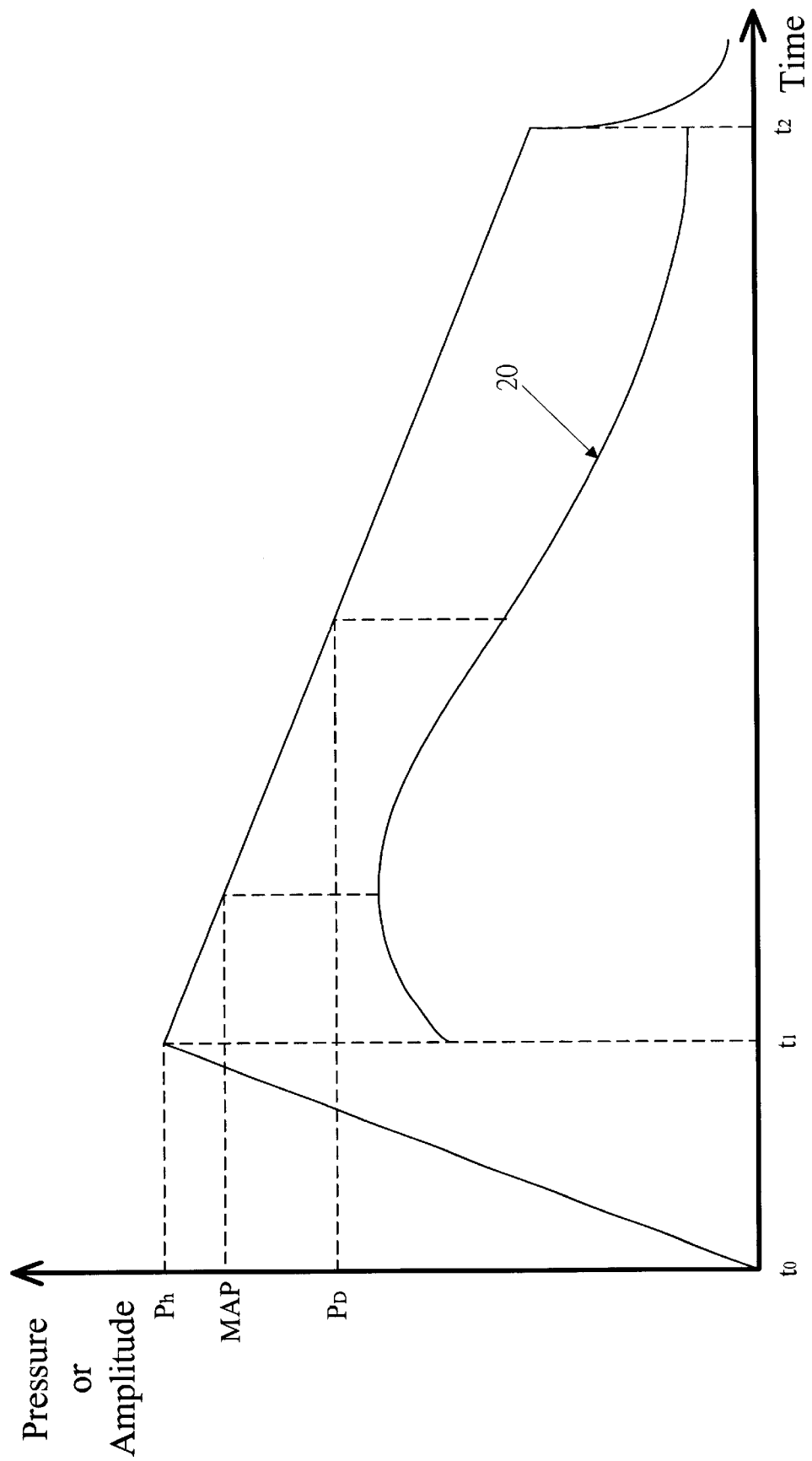
FIG. 2 shows two superimposed graphs of cuff pressure versus time and oscillation amplitudes versus time respectively demonstrating the present invention.
Figure 3:
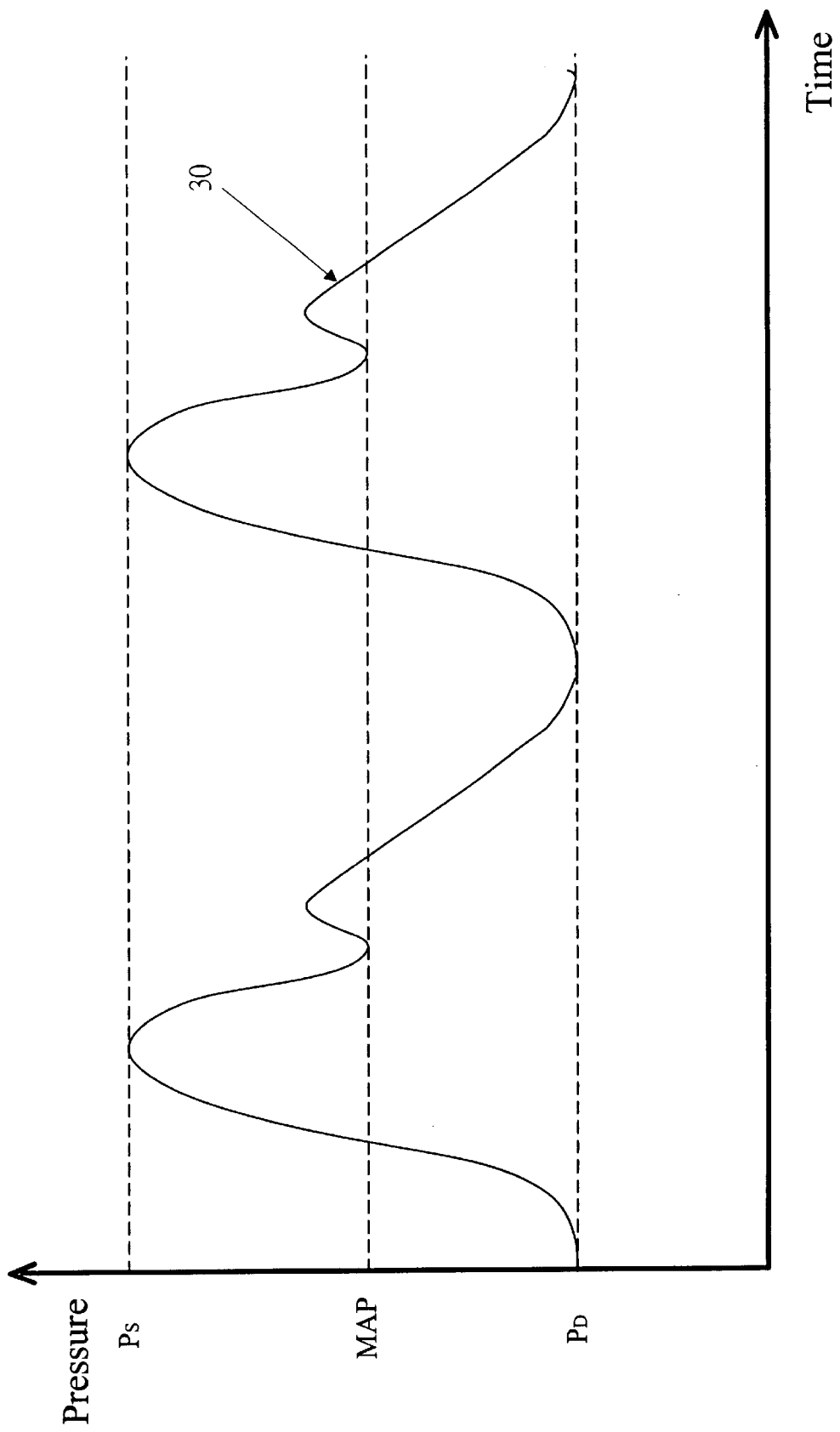
FIG. 3 is a graph of heart pulses pressure versus time.

In comparison, please turn to FIG. 2, the present invention is able to drop the maximum cuff inflation pressure in view of FIG. 3, a graph of the heart pulses, to provide a comfortable blood-pressure measurement. The lower graph of FIG. 2 corresponds to FIG. 1 with the left portion being truncated and the deflation process being shortened. In this embodiment, the enveloped curve 20 can determine blood pressure such as the diastolic pressure or the mean arterial pressure except for a systolic pressure. However, the systolic pressure can be further determined by referring to FIG. 3. The graph of FIG. 3 is preferably referred to with respect to the counterpressure pulses line 30 near the mean arterial pressure. The counterpressure pulses of this area are more stable to represent the actual heart pulses generated by the heart.

Theoretically, the muscles of the heart periodically contract to force blood through the arteries of the human. As a result, irregularly-shaped pressure pulses exist in theses arteries and cause them to flex or oscillate. The base line pressure for these pulses is the diastolic pressure $P_D$ and the peak pressure for these pulses is the systolic pressure $P_S$. A further pressure value, the mean arterial pressure MAP, represents a time-weighted average of the blood pressure. Accordingly, the systolic pressure can be determined based upon the diastolic pressure, the mean arterial pressure and the pulses 30.

The characteristic of the present invention is quite different from the prior blood-pressure determination because the measuring of systolic pressure in FIG. 1 cannot be predicted; therefore, the predetermined highest inflating cuff pressure must be fixed to a much higher value than the normal systolic pressure. However, for a majority of patients the systolic pressure is around 130 mmHg, more or less, while the inflating cuff pressure of prior methods has always been kept at 180 mmHg or above. It causes uncomfortable measurements even the inflation is applied rapidly. Moreover, it is not suitable for repeatedly measuring in consideration of the fatigue of the occluded blood vessel; otherwise the measurement may be incorrect. The highest inflating cuff pressure $P_h$ of the present invention depends on the MAP. As the cuff is inflated above the mean arterial pressure, the blood pressure can be determined. As such, for most users their MAP is around 110 mmHg, so the maximum value of the cuff pressure of the present invention need merely be above 110 mmHg to accomplish the measurement. As a result, if the difference between the systolic pressure and the mean arterial pressure is about 20 mmHg to about 40 mmHg, the present invention can provide a reduced inflation pressure during the blood-pressure measurement. Besides, the invention can employ a fuzzy logic control during the measuring process by predicting the mean arterial pressure. The prediction can be reached by monitoring arterial counterpressure oscillations at each pressure inflating process. As shown in the lower graph of FIG. 2, during the deflation process, the oscillation peak amplitudes will normally increase from a lower level to a relative maximum and, thereafter, will decrease. Similarly condition will occur during the inflation process although the oscillation amplitudes are difficult to detect. It is not necessary to obtain an accurate envelope curve like curve 20 but to take the changes of the oscillation amplitudes for reference so as to decide whether the maximum inflating pressure is above the mean arterial pressure. As such, the present invention can more precisely control and lower the maximum inflation pressure whereby the diastolic pressure and the mean arterial pressure can be reached.

Finally, an apparatus for measuring blood pressure according to the present invention method is provided. The apparatus includes an inflatable and deflatable cuff, a controller, a monitor, a pressure transducer, a processor and a calculator. The controller is used for controlling cuff pressure so as to inflate the cuff to a maximum cuff pressure higher than a predetermined value plus a predicted mean arterial pressure of a detected subject. The monitor detects arterial counterpressure pulses and oscillations at each of the cuff pressure deflating process. The pressure transducer is coupled to the cuff for converting the counterpressure oscillations to voltage signals. Next, the processor is used for processing the voltage signals into a sequence of peak amplitudes at each pressure deflating process, the sequence being enveloped by a curve containing a maximum value. The calculator first computes a diastolic pressure and a mean arterial pressure based upon the curve and then computes a systolic pressure based upon the diastolic pressure, the mean arterial pressure and the counterpressure pulses.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for measuring blood pressure, comprising:
   (a) applying a blood pressure cuff about a subject's limb containing an artery;
   (b) inflating the cuff to a cuff pressure above a predicted mean arterial pressure of the artery;
   (c) reducing the cuff pressure to permit an increasing flow of blood through the progressively less occluded artery;
   (d) monitoring arterial counterpressure pulses and oscillations during step (c);
   (e) converting the counterpressure oscillations to electrical signals;
   (f) processing the signals into a sequence of peak amplitudes having an envelope, the envelope defining a curve containing a maximum value;
   (g) determining a diastolic pressure and a mean arterial pressure based upon the curve; and
   (h) determining a systolic pressure based upon the diastolic pressure, the mean arterial pressure and the counterpressure pulses.

2. The method as set forth in claim 1, further comprising conducting step (b) through (h) repeatedly, and monitoring arterial counterpressure oscillations at each repetition to obtain a predicted mean arterial pressure, the pressure to which the cuff is inflated in repetitions of step (b) being selected on the basis of the predicted mean arterial pressure.

3. The method as set forth in claim 1, wherein the step (h) comprises computing the systolic pressure based upon the counterpressure pulses monitored around the mean arterial pressure.

4. The method as set forth in claim 1, wherein the curve has a segment ascending to the maximum value and a segment descending from the maximum value, wherein the diastolic pressure and the mean arterial pressure are determined during step (g) from the maximum value and the descending segment, and wherein step (c) is begun at a time such that the ascending segment of the curve is shorter than the descending segment and is insufficient for determining the systolic pressure.

5. A method for measuring blood pressure, comprising:
   (a) applying a blood pressure cuff about a subject's limb containing an artery;
   (b) inflating the cuff to a pressure above the mean arterial pressure of the artery;
   (c) reducing the cuff pressure to permit an increasing flow of blood through the artery;
   (d) measuring variations in the cuff pressure, as step (c) is conducted, to detect a sequence of pulse complexes, the sequence having an envelope with an ascending segment, a descending segment, and a maximum value between the ascending and descending segments, the descending segment of the envelope being substantially longer than the ascending segment;
   (e) determining a diastolic pressure and a mean arterial pressure based on the descending segment of the envelope and the maximum value;
   (f) monitoring the subject's pulse; and
   (g) determining a systolic pressure based on the pulse and the mean and diastolic pressures determined in step (e), wherein step (c) is begun at a time such that the descending segment of the envelope is substantially longer than the ascending segment, the ascending segment being insufficiently long for determining the systolic pressure.

\* \* \* \* \*